United States Patent [19]

Kallok

[11] Patent Number: 5,158,080
[45] Date of Patent: Oct. 27, 1992

[54] MUSCLE TONE

[75] Inventor: Michael J. Kallok, New Brighton, Minn.

[73] Assignee: Medtronic, Inc., Minneapolis, Minn.

[21] Appl. No.: 824,308

[22] Filed: Jan. 23, 1992

Related U.S. Application Data

[62] Division of Ser. No. 610,854, Nov. 8, 1990.

[51] Int. Cl.⁵ .............................................. A61N 1/36
[52] U.S. Cl. ..................................................... 128/421
[58] Field of Search ......................... 128/848, 421, 783

[56] References Cited

U.S. PATENT DOCUMENTS

| | | | |
|---|---|---|---|
| 4,519,400 | 5/1985 | Brenman et al. | 128/421 |
| 4,553,549 | 11/1985 | Pope et al. | 128/421 |
| 4,830,008 | 5/1989 | Meer | 128/421 |

Primary Examiner—William E. Kamm
Attorney, Agent, or Firm—Harold R. Patton; Daniel W. Latham; John L. Rooney

[57] ABSTRACT

An apparatus for and method of improving muscle tone of a patient using chronic sub-tetanic electrical stimulation. For patients suffering from obstructive sleep apnea, for example, the muscles of the upper airway are provided the chronic stimulation to mitigate or prevent the adverse medical condition caused in part by excessively flaccid muscle tissue around and in the airway.

A stimulation generator supplies pulses to the muscle to be treated through insulated leads which are coupled to electrodes directly in contact with the appropriate neuro-muscular tissue. The output of the stimulation generator is adjusted to a frequency of sufficiently low level as to prevent fused tetanic contraction of the stimulated muscle. The adjustment may be made manually by attending medical personnel or may be done automatically using electrodes to sense the tension of the stimulated muscle. In the automatic mode, the sensing system insures the stimulation frequency level is decreased below the threshold of muscle tetanus.

Stimulation may be accomplished at a particular site or may be multiplexed to a number of sites. Chronic stimulation will enhance muscle tone to an individual degree and then will simply maintain the desired status.

7 Claims, 8 Drawing Sheets

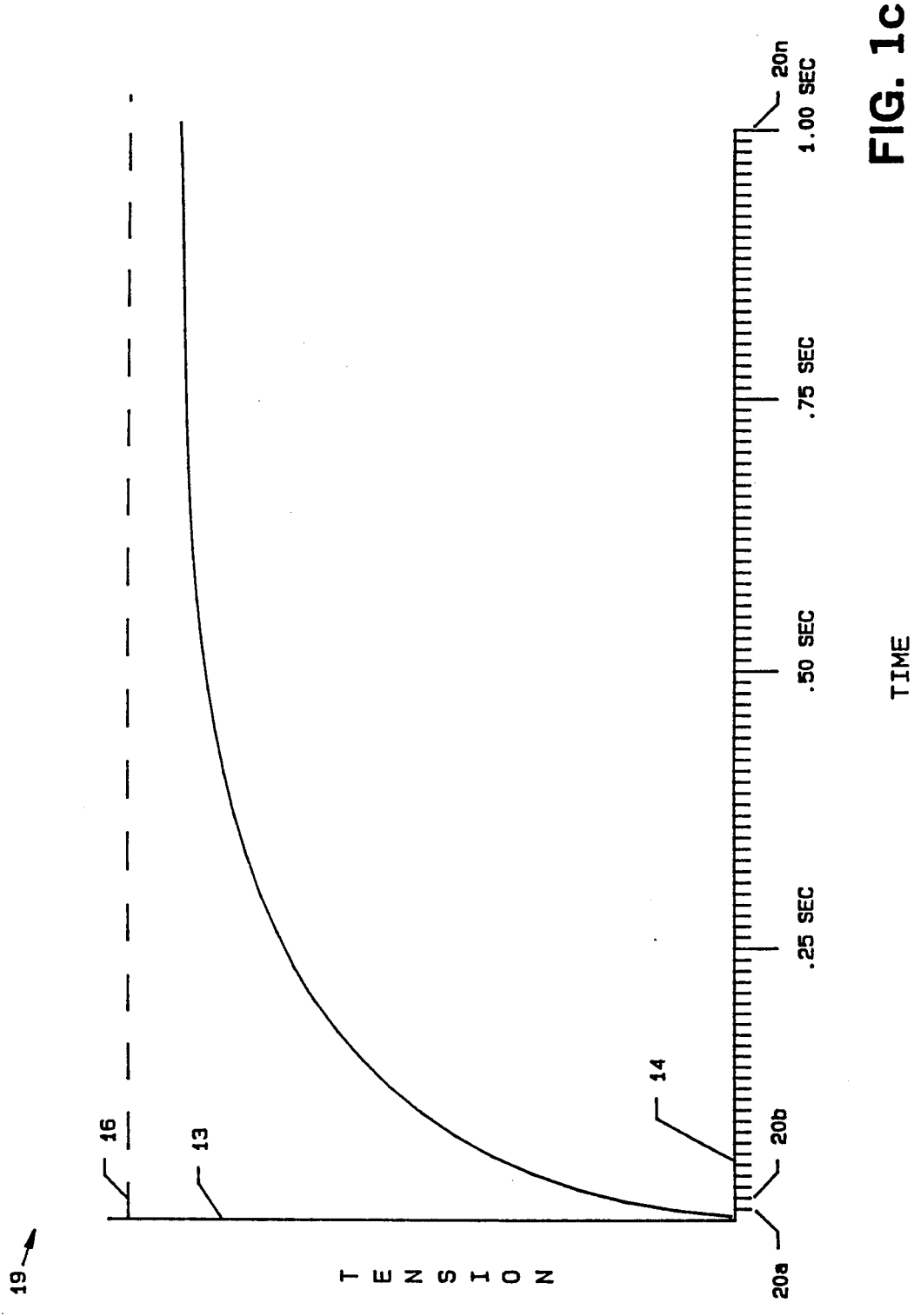

MUSCLE TONE

This is a divisional of copending application Ser. No. 07/610,854 filed on Nov. 8, 1990.

BACKGROUND OF THE INVENTION

1. Field of the Invention

The present invention generally relates to implantable medical devices, and more particularly, relates to implantable medical devices which provide non-tetanic stimulation of skeletal muscle tissue.

2. Description of the Prior Art

The medical characteristics of sleep apnea have been known for some time. There are two generally recognized forms of the disease. The first is central sleep apnea which is associated with the failure of the body to automatically generate the neuro-muscular stimulation necessary to initiate and control a respiratory cycle at the proper time. Work associated with employing electrical stimulation to treat this condition is discussed in "Diaphragm Pacing: Present Status", by William W. L. Glenn, in *Pace*, Volume I, at pages 357-370 (July-September 1978).

The second condition is known as obstructive sleep apnea. It is discussed at some length in "Obstructive Sleep Apnea: Diagnosis and Treatment", by Drs. Cook and Osguthorpe in *Journal of South Carolina Medical Association,* 81 (12): 647-651 (December, 1985). Additional references treating the subject include: "Physiologic Basis of Therapy for Sleep Apnea", by K. P. Strohl, N. S. Cherniack, and B. Gothe in *American Review of Respiratory Disease*, Volume 134, pp. 791-802 (1986); and "Obstructive Sleep Apnea Syndrome", by J. Kaplan and B. A. Staats in *Mayo Clinic Proceedings*, Volume 65, pp. 1087-1094 (1990).

Electrical stimulation of muscle tissue has been used for some time. Much work has been done in this area in cardiac pacing, for example. Paul E. Ciske and John A. Faulkner in "Chronic Electrical Stimulation of Nongrafted and Grafted Skeletal Muscles in Rats", in *Journal of Applied Physiology*, Volume 59(5), pp. 1434-1439 (1985), discuss some physiological effects of chronic stimulation.

At present, a tracheostomy may be the treatment of choice for a number of patients when obstructive sleep apnea is severe. However, some interest has been displayed in electrical stimulation of the muscle tissue along the upper airway during respiration. U.S. Pat. No. 4,830,008 issued to Meer discusses a technique for electrical stimulation of the muscles of the upper airway in synchrony with the respiratory cycle. U.S. Pat. No. 4,506,666 issued to Durkan discusses such stimulation in conjunction with pressurized airflow supplied by a respirator. A similar approach is discussed by Miki et al., in "Effects of Submental Electrical Stimulation During Sleep on Upper Airway Patency in Patients with Obstructive Sleep Apnea" in *American Review of Respiratory Disease*, Volume 140, pp. 1285-1289 (1989).

The electrical stimulation of the prior art techniques, however, are primarily concerned with causing contractile motion of the stimulated muscle. This means that the stimulation energy must necessarily be relatively large and the effects of the stimulation are directly cognizable by the patient.

SUMMARY OF THE INVENTION

The present invention overcomes the disadvantages of the prior art by providing a method and technique for treating medical conditions, such as obstructive sleep apnea, with non-tetanic stimulation. This stimulation is accomplished by pulses which are delivered at any amplitude sufficient to cause a muscle twitch, but at a frequency which is too slow to allow a fused tetanic contraction. The stimulation frequency is fast enough to result in an improvement in general muscle tone of the stimulated muscle without use of excess stimulation energy and without undue sensory stimulation of the patient. It is this general tightening of the musculature which provides the relief to the patient with obstructive sleep apnea by effectively stiffening the airway segment susceptible to collapse.

The stimulation pulses are supplied by a stimulation generator coupled through insulated electrical leads to electrodes in contact with the tissue to be stimulated. The frequency of the output pulses may be manually adjusted to prevent tetanus of the muscles to be stimulated.

Alternatively, the TENSION of the stimulated muscle tissue may be sensed by the stimulation generator. Special electronic circuitry can detect the muscle tone or tension and decrease the stimulation frequency to prevent contraction.

The technique may be practiced by stimulation at one or more sites. To facilitate multiple site stimulation, the output of the stimulation generator may be suitably demultiplexed.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1c is a graphical representation of muscle tension with 100 hertz stimulation;

DETAILED DESCRIPTION OF THE PREFERRED EMBODIMENTS

Figure 1A:
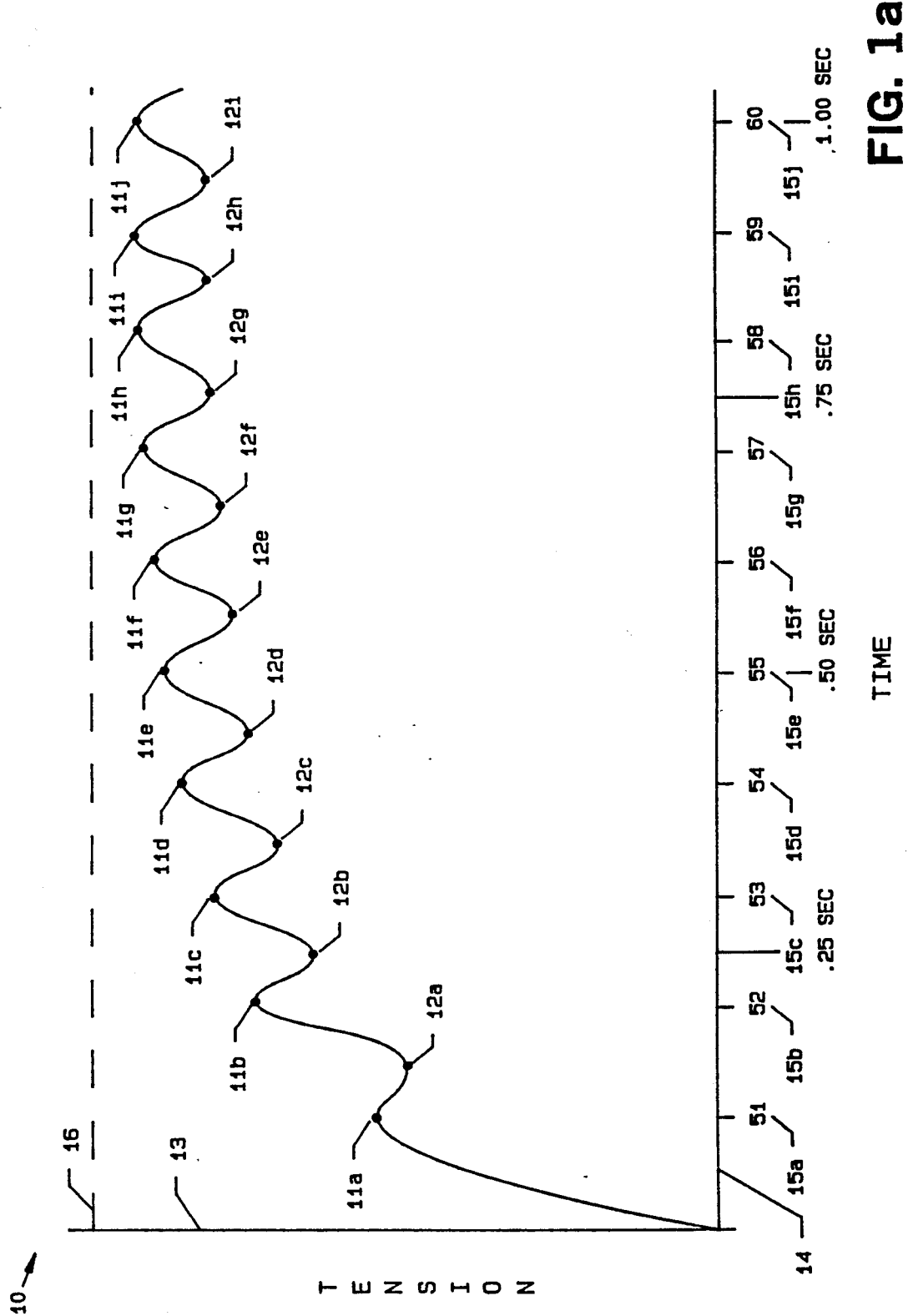
FIG. 1a is a graphical representation of muscle tension with 10 hertz stimulation.

FIG. 1a is a graphical representation 10 of muscle tension 13 as a function of time 14 under subthreshold stimulation at a rate of 10 pulses per second. The response produced is termed slow-twitch.

It can be seen that even though the tension produced tends to be cumulative, the relative peak associated with each stimulation pulse is prominently evident. As stimulation pulses 15a, 15b, 15c, 15e, 15f, 15g, 15h, 15i, and 15j cause the subject muscle to twitch, relative peaks 11a, 11b, 11c, 11d, 11e, 11f, 11g, 11h, 11i, and 11j, respectively, are produced. Relative troughs 12a, 12b, 12c, 12d, 12e, 12f, 12g, 12h, 12i, and 12j, respectively, are the corresponding troughs between stimulation pulses. Fused tetanic contraction 16 is the level of tension required to produce a fused tetanic contraction. Note that the stimulation pulses increase the muscle tension, but do not raise the tension to the level produced by a fused tetanic contraction. This general increase in tension acts to stiffen the stimulated muscles, but minimizes or eliminates the fatigue associated with a fused tetanic contraction.

Figure 1B:
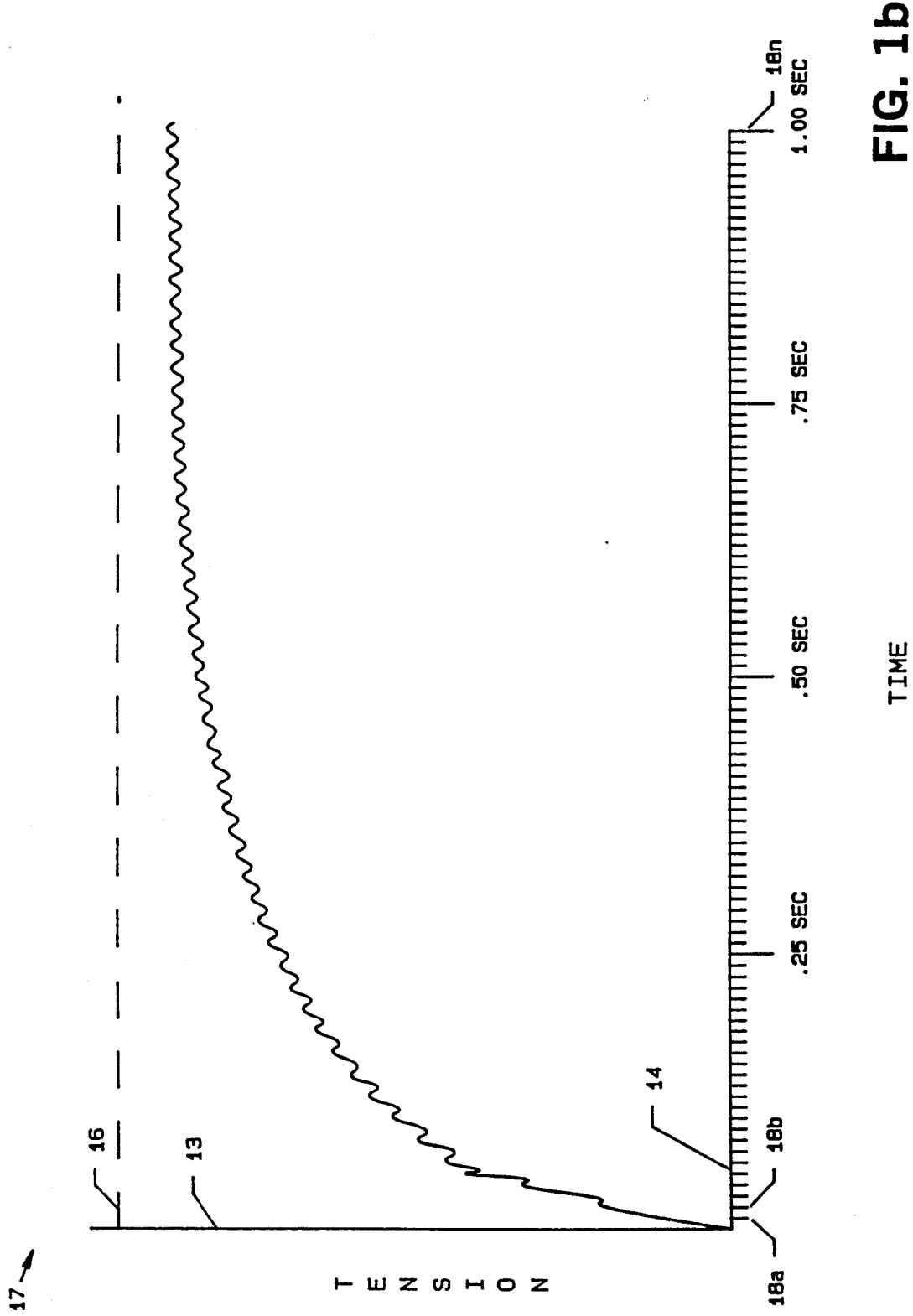
FIG. 1b is a graphical representation of muscle tension with 50 hertz stimulation.

FIG. 1b is a graphical representation 17 of muscle tension 13 as a function of time 14 under stimulation at a rate of 50 pulses per second. The term given to this reaction is non-fused tetanus. It can be seen that as each of the stimulation pulses 18a-18n is generated, the cumulative muscle response contains faintly pronounced relative maxima and minima. Also note that the level of tension reached is above the case shown in FIG. 1a, but below the level of tension for a fused tetanic contraction 16.

FIG. 1c is a graphical representation 19 of a fused tetanus response of the subject muscle. The muscle tension 13 as a function of time 14 results in a smooth, cumulative curve. Stimulation pulses 20a-20n are produced at the rate of 100 per second. No relative maxima and minima are present at this stimulation rate.

Figure 2:
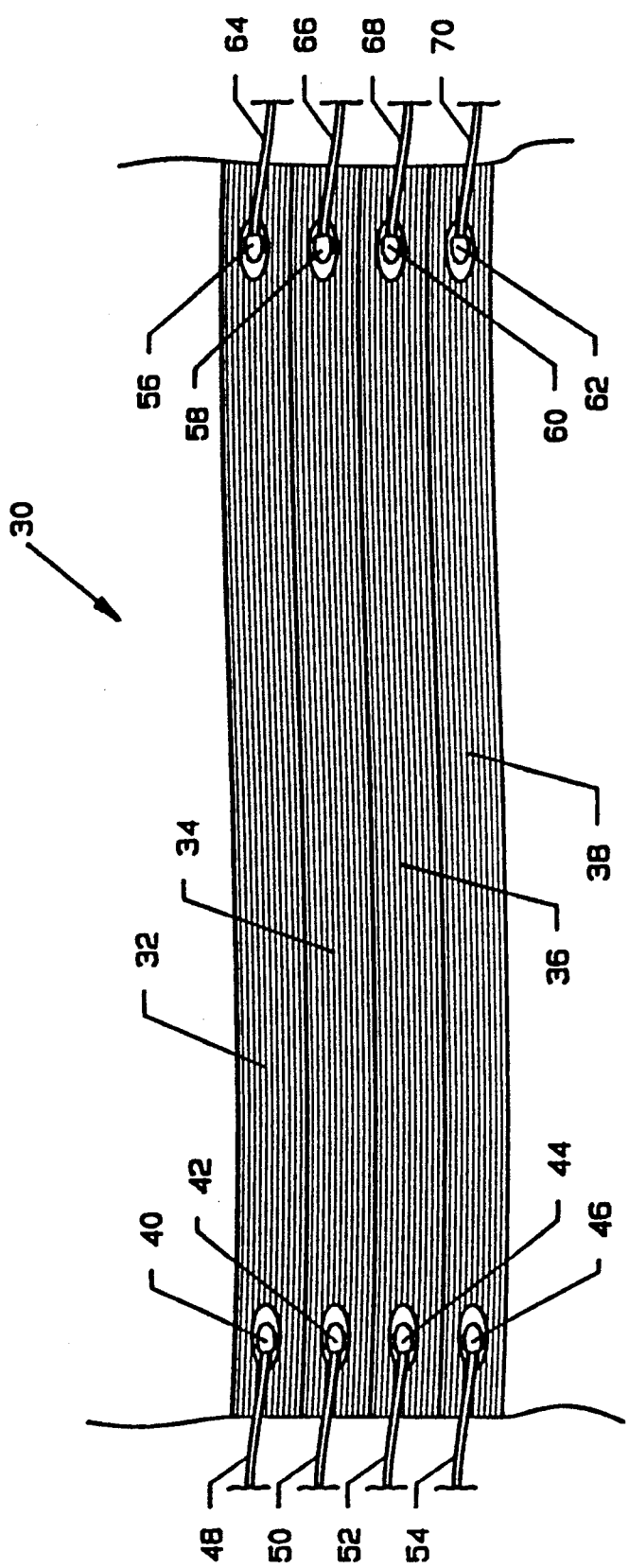
FIG. 2 is a view showing a typical arrangement of stimulation and sensing electrodes.

FIG. 2 shows the typical arrangement 30 of stimulation and sensing electrodes in a system having multiplexed inputs and outputs. Individual muscles 32, 34, 36, and 38 represent musculature of the upper airway in the obstructive sleep apnea patient. Typical muscle groups include genioglossus, thyrohyoid, sternohyoid, omohyoid, geniohyoid, mylohyoid, hypoglossus, stylohyoid, etc.

Electrodes 40, 42, 44, and 46 are stab-in electrodes such as Medtronic ® Model 4951. Each is coupled to the stimulation generator (see also FIG. 5) by a different one of insulated leads 48, 50, 52, and 54, respectively.

Electrodes 56, 58, 60, and 62 electrically coupled to insulated leads 64, 66, 68, and 70, respectively, may be of similar design and construction. Each of electrodes 56, 58, 60, and 62 senses the TENSION of the corresponding muscle 32, 34, 36, and 38. Electrodes other than the Medtronic ® Model 4951 may be used. Any electrode, metallic or conductive polymer, that is suitable for nerve or muscle stimulation, may be used to practice the present invention.

Figure 3:
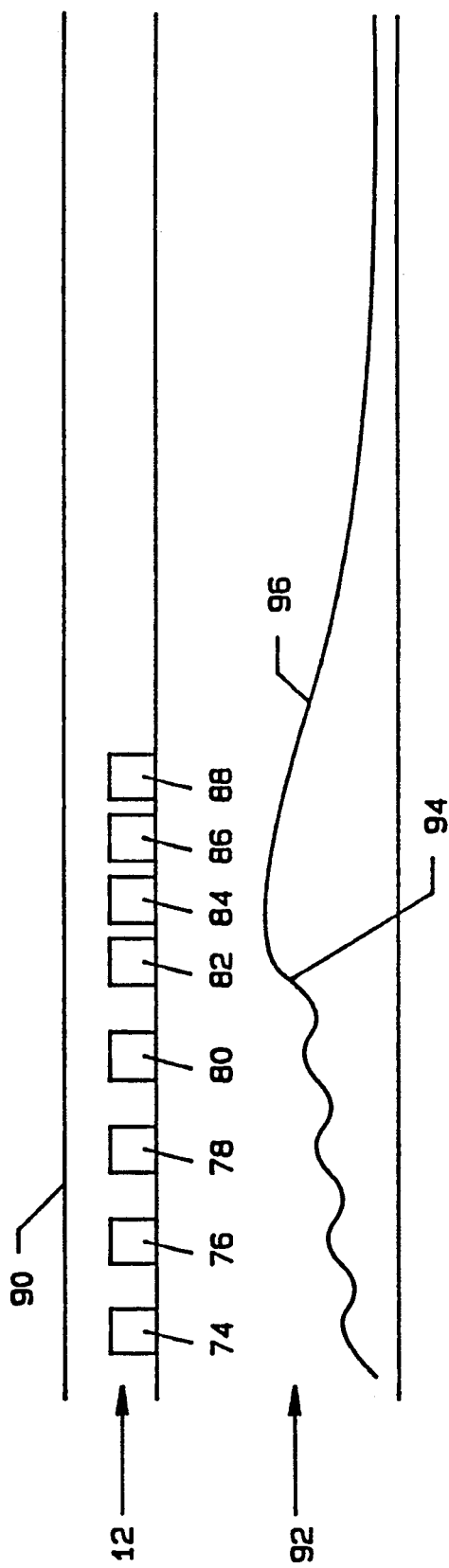
FIG. 3 is a qraphical representation of the sensed muscle tension for stimulation pulses above and below the fused tetanus frequency threshold.

FIG. 3 is a graphical representation of stimulation pulses which are both greater than and less than the frequency required for a fused tetanic contraction, along with the corresponding tension signal as sensed and integrated. Stimulation amplitude consists of individual pulses 74, 76, 78, 80, 82, 84, 86, and 88. Each has a pulse width of approximately 200-1000 microseconds. Individual pulses 74, 76, 78, and 80 have a lower frequency than the fused tetanic frequency. Similarly, each of the individual pulses 82, 84, 86, and 88 exceeds the frequency required for fused tetanic contraction.

Curve 92 shows the tension signal as sensed from the stimulated muscle and integrated into a smooth curve. The region prior to include 94 represents the integrated tension signal with the low frequency stimulation of pulses 74, 76, 78, and 80. The region of curve 92 between incline 94 and decline 96 is indicative of the integrated tension signal with pulses 82, 84, 86, and 88 sufficient to stimulate contraction.

Figure 4:
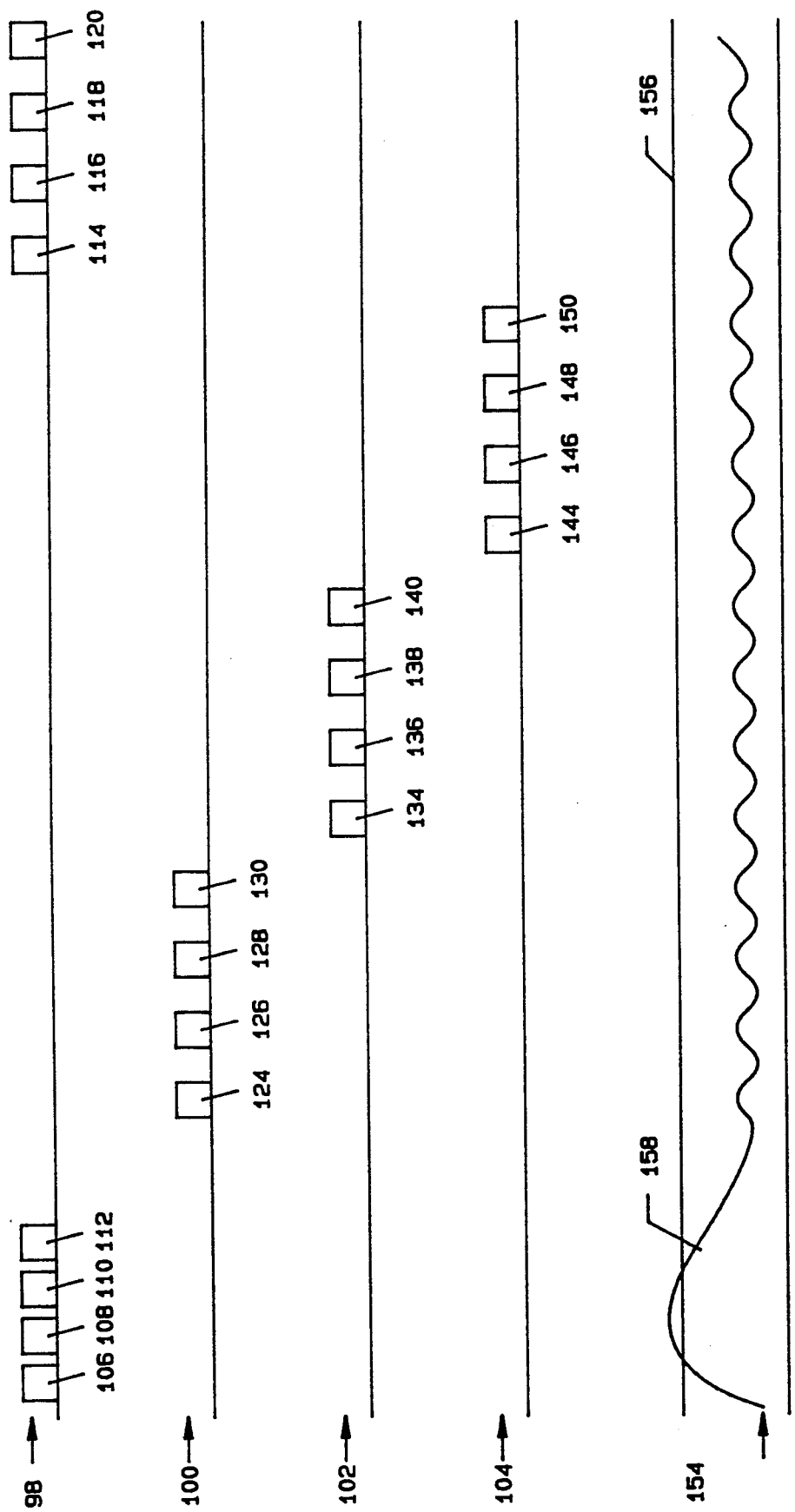
FIG. 4 is a graphical representation of the stimulation outputs and integrated sensed inputs of a multiplexed non-tetanic stimulation system.

FIG. 4 is a graphical representation of the operation of a multiplexed system having four separate inputs and outputs. Curve 98 shows stimulation pulses 106, 108, 110, 112, 114, 116, 118, and 120 applied to a first stimulation electrode (see also FIG. 2). Similarly, curves 100, 102, and 104 show the stimulation pulses applied to the second, third, and fourth stimulation electrodes, respectively. Curve 154 shows the integrated time multiplexed tension signal from the corresponding sensing electrodes.

Stimulation pulses 106, 108, 110, and 112 have a frequency high enough to result in a fused tetanic contraction. Therefore, region 158 of curve 154 indicates tetanus because it has tension greater than sensing threshold 156. This data is used by the stimulation generator as explained in greater detail below to lower the amplitude of the stimulation pulses to the corresponding muscle tissue.

Stimulation pulses 124, 126, 128, and 130 are of a lower frequency than stimulation pulses 106, 108, 110 and 112. Similarly, pulses 134, 136, 138, and 140 result in less tension than that resulting from pulses 106, 108, 110 and 112. Pulses 144, 146, 148, and 150 result in less tension than that resulting from pulses 106, 108, 110 and 112.

Figure 5:
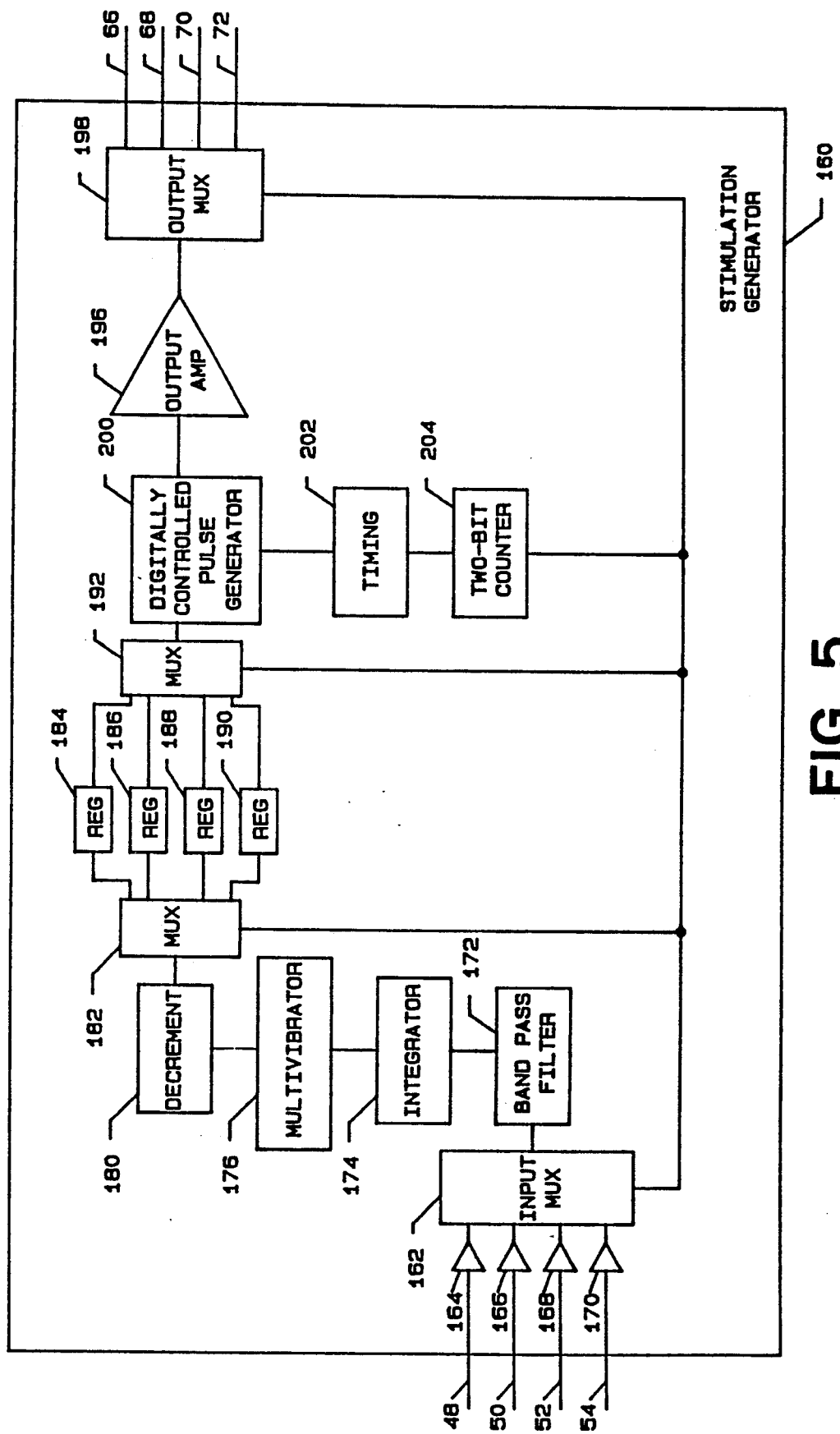
FIG. 5 is a block diagram of a stimulation generator having multiplexed inputs and outputs; and, FIG. 6 is a graphical representation of general muscle tone over time using chronic non-tetanic stimulation.

FIG. 5 is a block diagram of stimulation generator 160 which supplies the stimulation pulses of FIG. 4 and also performs the sensing function. Sensing inputs are received from insulated leads 48, 50, 52, and 54, and stimulation pulses are output via insulated leads 66, 68, 70, and 72 (see also FIG. 2).

The individually sensed tension signals are amplified by sense amplifiers 164, 166, 168, and 170, respectively. Input mux 162 time division multiplexes the signals in accordance with the output of recycling two-bit counter 204 which is driven by the ten millisecond output of timing 202.

In turn, each of the amplified tension signals is output from input mux 162 to band pass filter 172. The output of band pass filter 172 severely attenuates components over one megahertz. The output is integrated by integrator 174 to provide the smooth signal discussed above (see also curve 92 of FIG. 3). Multivibrator 176 thresholds this signal to determine if the sensed tension indicates tetanus as explained above. If yes, decrement 180 is enabled to decrement the corresponding one of registers 184, 186, 188, and 190 through mux 182. If no, decrement 180 is not enabled.

Mux 182 supplies the contents of the proper one of registers 184, 186, 188, and 190 to control the frequency of pulses generated by digitally controlled pulse generator 200. This ensures that the corresponding stimulation pulses which are output will be sub-tetanus. The pulses are generated by pulse generator 200 based upon timing 202 which enables synchrony with the multiplexer activity. Output amplifier 196 is a linear amplifier which provides the proper output amplitude. Output mux 198 selects the proper stimulation electrode for the stimulation pulses.

Figure 6:
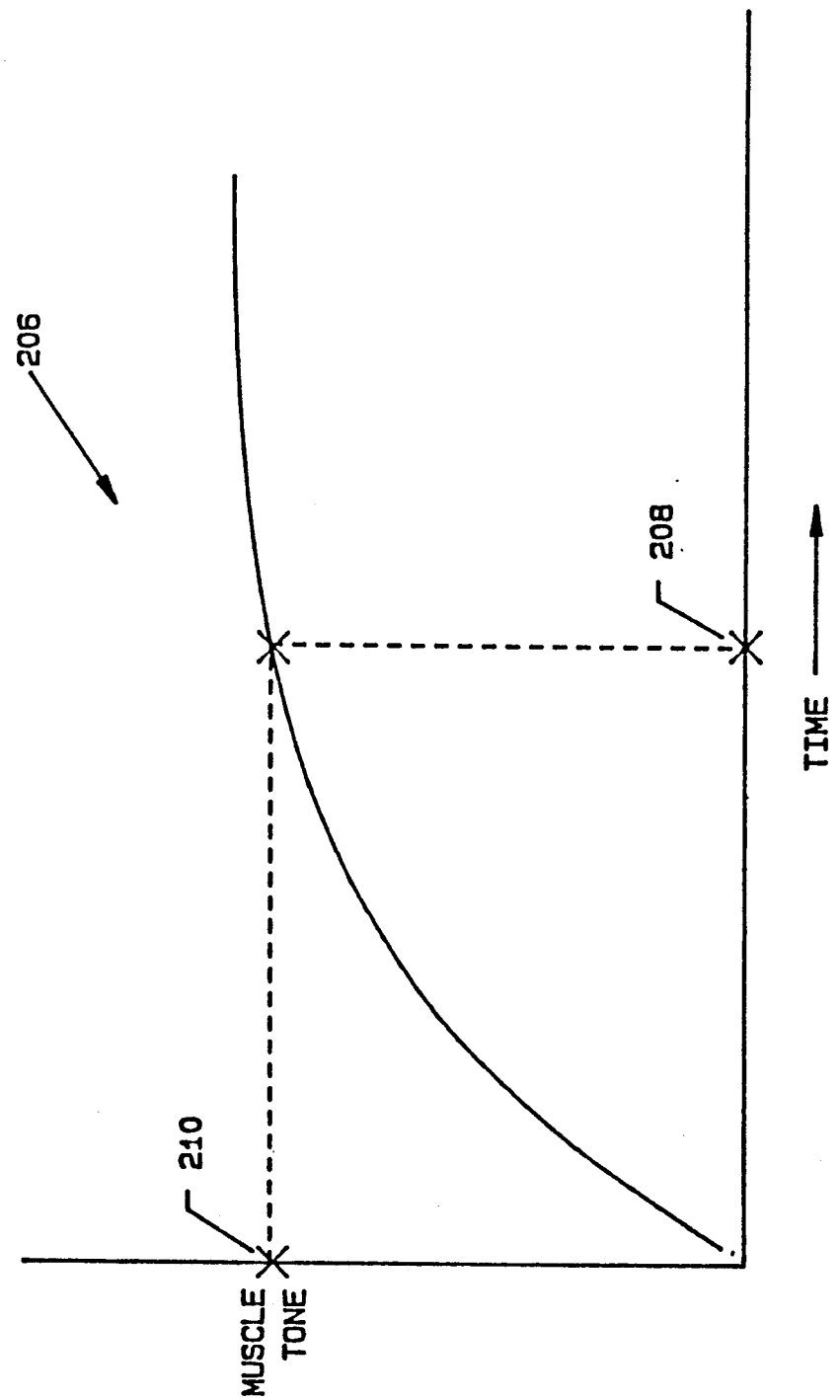

FIG. 6 is a graphical representation 206 of the general muscle tone 210 as a function of the period of sub-tetanic stimulation 208. Note that following a sub-tetanic stimulation period 208, the general muscle tone does not appreciably increase and the continued sub-tetanic stimulation serves to maintain the level of muscle tone. Since the stimulation frequency is reduced, providing a "rest period" between stimuli, muscle fatigue is reduced or eliminated, but an increased level of tone is reached.

Having thus described the preferred embodiments of the present invention, those of skill in the art will be readily able to appreciate the additional useful embodiments which may be utilized without departing from the scope of the claims hereto attached.

I claim:

1. A method of treating obstructive sleep apnea comprising:
   a. coupling electrodes to muscle tissue of the upper airway; and
   b. chronically stimulating said muscle tissue at a stimulus level of less than that producing fused tetanic contraction.

2. A method according to claim 1 further comprising: chronically monitoring said muscle tissue of said upper airway for occurrence of fused tetanic contraction.

3. A method according to claim 2 further comprising: decreasing frequency of said stimulation of said muscle tissue if said chronically monitoring step indicates fused tetanic contraction.

4. An apparatus for treating obstructive sleep apnea comprising:
   a. an electrode coupled to muscle tissue of the upper airway of a patient;
   b. means coupled to said electrode for supplying stimulation pulses to said muscle tissue via said electrode;
   c. means coupled to said muscle for sensing tetanic contraction of said muscle tissue; and
   d. means coupled to said sensing means and said supplying means for adjusting said stimulation pulses in response to said supplying means to ensure that said stimulation pulses do not stimulate fused tetanic contraction of said muscle tissue.

5. An apparatus according to claim 4 wherein said adjusting means further comprises means for decreasing the frequency of said stimulation pulses.

6. An apparatus according to claim 5 further comprising a plurality of electrodes coupled to said supplying means.

7. An apparatus according to claim 6 wherein said adjusting means further comprises means for increasing said frequency of said stimulation pulses.

* * * * *

UNITED STATES PATENT AND TRADEMARK OFFICE
CERTIFICATE OF CORRECTION

PATENT NO. : 5,158,080
DATED : October 27, 1992
INVENTOR(S) : Michael J. Kallok

It is certified that error appears in the above-indentified patent and that said Letters Patent is hereby corrected as shown below:

Title page, item [54] and col. 1, line 1,
In the title, "MUSCLE TONE" should be replaced with --METHOD OF AND APPARATUS FOR TREATING OBSTRUCTIVE SLEEP APNEA--.

Column 3, line 69, "include" should be --incline--.

Signed and Sealed this

Twentieth Day of September, 1994

Attest:

BRUCE LEHMAN

*Attesting Officer*  *Commissioner of Patents and Trademarks*